(12) United States Patent
Köcher

(10) Patent No.: US 7,064,231 B2
(45) Date of Patent: Jun. 20, 2006

(54) OPTICALLY ACTIVE DIAMINES AND THEIR USE IN CATALYTIC PROCESSES

(75) Inventor: Jürgen Köcher, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/643,855

(22) Filed: Aug. 19, 2003

(65) Prior Publication Data

US 2004/0044238 A1    Mar. 4, 2004

(30) Foreign Application Priority Data

Aug. 21, 2002  (DE)  ................ 102 38 114

(51) Int. Cl.
| | |
|---|---|
| C07C 27/00 | (2006.01) |
| C07C 255/04 | (2006.01) |
| C07C 229/24 | (2006.01) |
| C07C 229/26 | (2006.01) |
| C07F 9/40 | (2006.01) |

(52) U.S. Cl. ............ 560/125; 560/38; 558/390; 558/430; 564/15; 568/814

(58) Field of Classification Search ........... 558/390, 558/430; 560/38, 125; 564/15; 568/814
See application file for complete search history.

(56) References Cited

U.S. PATENT DOCUMENTS

| | | | |
|---|---|---|---|
| 4,165,330 A | 8/1979 | Whitney et al. | ...... 260/448.2 B |
| 5,227,538 A | 7/1993 | Buchwald et al. | ......... 568/814 |
| 6,245,952 B1 | 6/2001 | Mimoun | ...................... 568/814 |
| 6,392,103 B1 | 5/2002 | Mimoun | ...................... 568/814 |
| 6,533,960 B1 | 3/2003 | Mimoun | .................. 252/188.1 |
| 6,573,395 B1 | 6/2003 | Mimoun | ...................... 556/127 |
| 2002/0161252 A1 | 10/2002 | Mimoun | ...................... 556/118 |

FOREIGN PATENT DOCUMENTS

WO    00/24751    5/2000

OTHER PUBLICATIONS

Database CAPLUS on STN, Acc. No. 1983:540045, Horner et al., Phosphorus and Sulfur and the Related Elements (1983) 15(3), p. 331-49 (abstract).*

Two Isomeric Cyclohexylcyclams; Polyhedron, Bd. 17, Nr. 9, 1998, Seiten 1463-1470, EX0001156620; * Beispeil lt*.

J. Am. Chem. Soc. month unavailable 1994, 116, pp. 11667-11670; M.B. Carter, B. Schiott, A. Gutierrez and S.L. Buchwald; "Enantioselective Hydrosilylation of Ketones with a Chiral Titanocene Catalyst".

J. Am. Chem. Soc. month unavailable 1999, pp. 6158-6166; H. Mimoun, J. Yves de Saint Laumer, L. Giannini, R. Scopelliti and C. Floriani; "Enantioselective Reduction of Ketones by Polymethyl hydrosiloxane in the Presence of Chiral Zinc Catalysts".

J. Am. Chem. Soc., 1999 Supporting Info pp. 1-35.

* cited by examiner

Primary Examiner—Brian Davis
(74) Attorney, Agent, or Firm—Jill Denesvich

(57) ABSTRACT

The invention relates to stereoisomerically enriched diamines, to metal complexes comprising these diamines and also to their use in a process for asymmetrically reducing ketones using silanes, in particular polymethylhydrosiloxane, as reducing agents.

16 Claims, No Drawings

OPTICALLY ACTIVE DIAMINES AND THEIR USE IN CATALYTIC PROCESSES

BACKGROUND OF THE INVENTION

1. Field of the Invention

The invention relates to stereoisomerically enriched diamines, to metal complexes comprising these diamines and also to their use in a process for asymmetrically reducing ketones using silanes, in particular polymethylhydrosiloxane, as reducing agents.

2. Brief Description of the Prior Art

As a consequence of the steadily growing significance of stereoisomerically enriched alcohols as fine chemicals, active ingredients in agrochemicals and pharmaceuticals or their intermediates and also their aromas and scents, the asymmetric reduction of ketones has found technical use on the industrial scale.

The focus is directed in particular to the development of catalysts which facilitate high yields and conversion rates at high stereoselectivities. U.S. Pat. No. 5,227,538 and J. Am. Chem. Soc. 116 (1994), 11667 disclose processes in which the asymmetric reduction of ketones using silanes in the presence of a titanium complex are carried out using optically active ligands as catalysts. A disadvantage of these processes is the high cost of the catalysts required in a large amount, which is in the range of 5 mol %, based on the ketone used.

WO-A 99/50211, WO-A 99/12877 and J. Am. Chem. Soc. 1999, 121, 6158 disclose processes for asymmetrically reducing ketones which use polymethylhydrosiloxane (PHMS) as an inexpensive reducing agent and metal hydrides as catalysts, which are formed from a metal salt or a metal complex by a reducing agent. The asymmetric induction is effected by stereoisomerically enriched, secondary 1,2-diamines as ligands. A disadvantage of this method is the fact that this process only achieves moderate optical yields of the alcohols of 70 to 80%.

There was therefore a need to develop further catalysts and ligands which facilitate the asymmetric reduction of ketones in good yields and good optical purities.

SUMMARY OF THE INVENTION

In accordance with the foregoing, the present invention encompasses compounds of the formula (I)

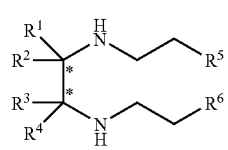

(I)

where

* marks stereogenic carbon atoms which each independently have R— or S— configuration, excluding meso-compounds and $R^1$, $R^2$, $R^3$ and $R^4$ are each independently hydrogen, $C_1$–$C_{12}$-alkyl, $C_4$–$C_{24}$-aryl or $C_5$–$C_{25}$-arylalkyl, or $R^1$, $R^2$, $R^3$ and $R^4$ together with the ethylene bridge are 1,2-($C_5$–$C_8$-cycloalkyl) and $R^5$ and $R^6$ are each independently radicals which are selected from the group of —$COOR^7$, —$CONR^8R^9$, —CN or —$PO(OR^{10})_2$ where $R^7$, $R^8$, $R^9$ and $R^{10}$ are each $C_1$–$C_{12}$-alkyl, $C_4$–$C_{24}$-aryl or $C_5$–$C_{25}$-arylalkyl, or $NR^8R^9$ as a whole is a cyclic amino radical having a total of 4 to 12 carbon atoms.

For the purposes of the invention, all radical definitions, parameters and illustrations hereinabove and listed hereinbelow, in general or within areas of preference, and thus also the particular areas and areas of preference, may be combined as desired.

DETAILED DESCRIPTION OF THE INVENTION

The compounds of the formula (I) have different stereoisomers. The invention encompasses both the pure stereoisomers and any desired mixtures of stereoisomers, for example racemates.

Alkyl is in each case independently a straight-chain, cyclic, branched or unbranched alkyl radical. The same applies to the nonaromatic moiety of an aryl-alkyl radical.

$C_1$–$C_4$-Alkyl is, for example, methyl, ethyl, n-propyl, isopropyl, n-butyl, sec-butyl and tert-butyl, $C_1$–$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-l-methylpropyl, 1-ethyl-2-methylpropyl, 1-ethyl-2-methylpropyl, n-heptyl and n-octyl, and $C_1$–$C_{12}$-alkyl is further additionally, for example, adamantyl, n-nonyl, n-decyl and n-dodecyl.

Aryl is in each case independently aromatic or a heteroaromatic radical having 4 to 24 framework carbon atoms, of which no, one, two or three framework carbon atoms per cycle, but at least one framework carbon atom in the entire molecule, may be substituted by heteroatoms selected from the group of nitrogen, sulphur or oxygen, but is preferably a carbocyclic aromatic radical having 6 to 24 framework carbon atoms.

Examples of carbocyclic aromatic radicals having 6 to 24 framework carbon atoms are phenyl, naphthyl, phenanthrenyl, anthracenyl or fluorenyl, and hetero-aromatic radicals having 4 to 24 framework carbon atoms, of which no, one, two or three framework carbon atoms per cycle, but at least one framework carbon atom in the entire molecule, may be substituted by heteroatoms selected from the group of nitrogen, sulphur or oxygen, are, for example, pyridinyl, benzofuranyl, dibenzofuranyl or quinolinyl.

The carbocyclic aromatic radical or heteroaromatic radical may also be substituted by up to five identical or different substituents per cycle which are selected from the group of chlorine, fluorine, $C_1$–$C_{12}$-alkyl, $C_1$–$C_{12}$-alkoxy, di($C_1$–$C_8$-alkyl)amino, COO($C_1$–$C_8$-alkyl), CON($C_1$–$C_8$-alkyl)$_2$, COO($C_1$–$C_8$-alkyl), COO($C_4$–$C_{14}$-aryl), CO($C_1$–$C_8$-alkyl), $C_5$–$C_{15}$-arylalkyl or tri($C_1$–$C_6$-alkyl)siloxyl.

$C_4$–$C_{24}$-Aryl is, for example and with preference, phenyl, o-, p-, m-tolyl, o-, p-, m-anisyl, o-, p-, m-fluorophenyl, o-, p-, m-chlorophenyl, o-, p-, m-trifluoro-methylphenyl, o-, p-, m-nitrophenyl and 2-, 3- and 4-pyridyl.

Arylalkyl is in each case independently a straight-chain, cyclic, branched or unbranched alkyl radical as defined above which may be singly, multiply or fully substituted by aryl radicals as defined above.

$C_5$–$C_{15}$-Arylalkyl is, for example and with preference, benzyl or (R)— or (S)-1-phenylethyl.

The preferred substitution patterns for compounds of the formula (I) are defined hereinbelow:

$R^1$, $R^2$, $R^3$ and $R^4$ are preferably each independently hydrogen, $C_1$–$C_8$-alkyl or $C_4$–$C_{24}$-aryl, or $R^1$, $R^2$, $R^3$ and $R^4$ together with the ethylene bridge are each 1,2-cyclohexylene.

$R^1$, $R^2$, $R^3$ and $R^4$ together with the ethylene bridge are particularly preferably 1,2-dimethyl-1,2-ethylene, 1,2-diphenyl-1,2-ethylene or 1,2-cyclohexylene, very particularly preferably (R,R)— and (S,S)-1,2-diphenyl-1,2-ethylene or (R,R)— and (S,S)-1,2-cyclohexylene.

$R^5$ and $R^6$ are preferably each independently, but more preferably identically, radicals selected from the group of —$COOR^7$, —$CONR^8R^9$, —CN or —$PO(OR^{10})_2$, where $R^7$, $R^8$, $R^9$ and $R^{10}$ are each $C_1$–$C_4$-alkyl or $C_4$–$C_{24}$-aryl.

$R^5$ and $R^6$ are each very particularly preferably —$COOCH_3$, —$COOC_2H_5$, —CN, —$CON(CH_3)_2$, –$CON(C_2H_5)_2$, —$PO(OCH_3)_2$, —$PO(OC_2H_5)_2$ and —$PO(Ophenyl)_2$.

Particularly preferred compounds of the formula (I) are as follows:

(1S,2S)- and (1R,2R)-bis-[N-(2-dimethylphosphonatoethyl)amino]cyclohexane, (1S,2S)- and (1R,2R)-bis-[N-(2-diethylphosphonatoethyl)amino]cyclohexane, (1S,2S)- and (1R,2R)-bis-[N-(2-diphenylphosphonatoethyl)amino]cyclohexane, (1S,2S)- and (1R,2R)-bis-[N-(2-cyanoethyl)amino]cyclohexane, (1S,2S)- and (1R,2R)-bis-[N-(2-carboxylethylethyl)amino]cyclohexane and (1S,2S)- and (1R,2R)-bis-[N-(2-carboxylmethylethyl)amino]cyclohexane, (1S,2S)- and (1R,2R)-bis-[N-(2-dimethylphosphonatoethyl)amino]-1, 2-diphenylethane, (1S,2S)- and (1R,2R)-bis-[N-(2-diethylphosphonatoethyl)amino]-1,2-dipenylethane, (1S,2S)- and (1R,2R)-bis-[N-(2-dipenylphosphonatoethyl)amino]-1,2-diphenylethane, (1S,2S)- and (1R,2R)-bis-[N-(2-cyanoethyl)amino]-1,2-diphenylethane, (1S,2S)- and (1R,2R)-bis-[N-(2-carboxyethylethyl)amino]-1,2-diphenylethane, (1S,2S)- and (1R,2R)-bis-[N-(2-carboxymethylethyl)amino]-1,2-diphenylethane.

The compounds of the formula (I) according to the invention can be prepared in a manner known per se (see WO-A 00/24751), for example, by reacting amines of the formula (II)

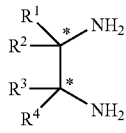  (II)

where

*, $R^1$, $R^2$, $R^3$ and $R^4$ are each as defined under formula (I), including their areas of preference, with compounds of the formula (III)

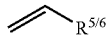  (III)

where $R^5$ and $R^6$ are each as defined under formula (I), including their areas of preference.

The invention also encompasses catalysts which comprise transition metal complexes of compounds of the formula (I).

The ratio of transition metal to compound of the formula (I) is preferably 0.05 to 2.0, particularly preferably 0.1 to 1.5 and very particularly 0.9 to 1.1.

Transition metal complexes of compounds of the formula (I) are preferably zinc and cobalt complexes of compounds of the formula (I).

Particularly preferred transition metal complexes of compounds of the formula (I) are those which are obtainable by reacting halides, carbonates, cyanurates, isocyanates, sulphates, phosphates, nitrates, carboxylates or alkoxides of zinc or cobalt with compounds of the formula (I).

Such transition metal complexes are preferably reacted with reducing agents before they are used as a catalyst. Examples of suitable reducing agents include hydrides of alkali metals and alkaline earth metals or aluminum-hydrogen or boron-hydrogen compounds, in particular those of the formula (IV)

$$\text{Met}[E\ H_qR^{11}{}_{(4-q)}]_p \quad\quad (IV)$$

where

Met is a mono- or bivalent metal, preferably zinc, lithium, sodium or potassium and E is aluminum or boron and $R^{11}$ is $C_1$–$C_8$-alkyl and q is 1, 2, 3 or 4, preferably 4 or 1, and p is the valency of Met.

Very particularly preferred reducing agents are $LiBH_4$, $NaBH_4$, $Zn(BH_4)_2$, $LiAlH_4$, $Li[BHethyl_3]$ and $Li[AlH(sec-butyl)_3]$, $Na[AlH_2(2$-methoxyethoxy$)_2]$, sodium hydride and lithium hydride.

The amount of the reducing agent is preferably selected in such a way that the molar ratio of hydridic hydrogen in the reducing agents to the transition metal complex is 0.5 to 5. Larger ratios are possible but uneconomic.

Further particularly preferred transition metal complexes are those which are obtained by reacting compounds of the formula (I) with zinc compounds $ZnY_2$ or ZnYHal where Y is in each case independently hydrogen, $BH_4$ or an organic radical, for example and with preference, $C_1$–$C_8$-alkyl phenyl, and Hal is bromine, chlorine or iodine.

Preferred zinc compounds $ZnY_2$ are dimethylzinc, diethylzinc, dibutylzinc, diphenylzinc and zinc hydride. Examples of preferred zinc compounds ZnYHal are phenylzinc chloride, methylzinc chloride and ethylzinc chloride.

These further preferred transition metal complexes can be used directly as catalysts.

The invention also encompasses a process for asymmetrically reducing ketones with silanes in the presence of catalysts, which is characterized in that the catalysts used are those which comprise transition metal complexes of compounds of the formula (I).

The definitions, including their areas of preference, specified for the transition metal complexes and for the compounds of the formula (I) apply correspondingly.

Transition metal complexes of compounds of the formula (I) can either be used as isolated complexes or, in a preferred procedure, prepared directly in the reaction mixture.

Preferred silanes are those of the formula (V)

$$H_rSiCl_s(C_1\text{–}C_8\text{-alkyl})_t(C_1\text{–}C_8\text{-alkoxy})_u(\text{phenyl})_v \quad\quad (V)$$

where r is one, two or three and $(s+t+u+v)=(4-r)$ or polymethylhydrosiloxane (PMHS) having the repeating structural unit

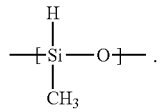

Particular preference is given to $H_2Si(C_1\text{–}C_8\text{-alkyl})_2$, $HSi(C_1\text{–}C_8\text{-alkoxy})_3$, $H_rSiCl_s(C_1\text{–}C_8\text{-alkyl})_t$, $HSiphenyl_3$, $H_2Siphenyl_2$, $H_3Siphenyl$ and PMHS, and even greater preference is given to PMHS.

The amount of catalyst is advantageously selected in such a way that the molar ratio of transition metal, preferably zinc, to ketone used is 0.001 to 0.20, preferably 0.01 to 0.1 and particularly preferably 0.01 to 0.05. The reaction temperature is, for example, −20° C. to 120° C., preferably 0° C. to 60° C.

The reaction can be carried out with or without, preferably with, solvent. Examples of useful solvents include ethers such as methyl tert-butyl ether, dioxane, tetrahydrofuran, ethylene glycol dimethyl ether or diisopropyl ether and also aliphatic or aromatic hydrocarbons, for example cyclohexane, toluene, n-hexane, n-heptane, petroleum ether, xylene or mesitylene.

Preferred ketones are aryl ketones, in particular optionally substituted acetophenones, propiophenones or butyrophenones.

In the manner according to the invention, stereoisomerically enriched alcohols are obtained.

The stereoisomerically enriched alcohols which can be obtained according to the invention are suitable in particular in a process for preparing pharmaceuticals and agrochemicals.

The advantage of the invention is that ligands and their transition metal complexes are provided which can be prepared in a simple manner and allow high yields and stereoselectivities in the asymmetric reduction of ketones.

EXAMPLES

Example 1

Preparation of (1S,2S)-bis-[N-(2-cyanoethyl)amino]cyclohexane

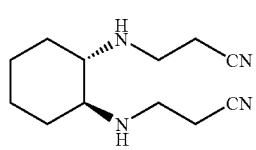

1.0 g of (1S,2S)-(+)-diaminocyclohexane (8.8 mmol) is dissolved at room temperature in 10 ml of ethanol. 1.24 ml of acrylonitrile (1.0 g, 18.8 mmol) are added and the mixture is stirred at room temperature for 72 h. According to gas chromatography analysis, the diaminocyclohexane has been completely converted. After distillation of the alcohol, a colorless oil (1.8 g) remains which, according to gas chromatography analysis, is a homogeneous product (purity >98%).

Example 2

Preparation of (1S,2S)-bis-[N-(2-cyanoethyl)amino]-1,2-diphenylethane

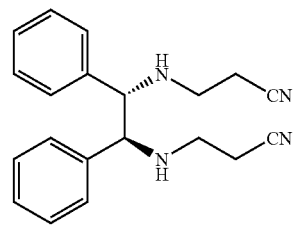

0.5 g of (1S,2S)-(−)-diphenylethylenediamine (2.4 mmol) is dissolved in 10 ml of ethanol. After the addition of 0.32 ml of acrylonitrile (4.9 mmol), the mixture is stirred at room temperature for 20 h. After this time, another 0.1 ml of acrylonitrile (0.08 g, 1.5 mmol) is added and the mixture is stirred at room temperature for a further 72 h. The solvent is distilled off and the remaining oil is admixed with 5 ml of ether. The precipitated solid (0.46 g) is filtered off with suction and dried under high vacuum. According to gas chromatography analysis, the product has a purity of 99%.

Example 3

Preparation of (1S,2S)-bis-[N-(2-carboxylethyl-ethyl)amino]cyclohexane

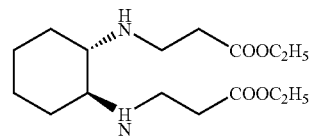

1.0 g of (1S,2S)-(−)-diaminocyclohexane (8.8 mmol) is dissolved in 50 ml of ethanol, then 2.0 ml of ethyl acrylate (1.84 g, 18.4 mmol) are added. The mixture is stirred at room temperature for 24 h. According to gas chromatography analysis, the reactant has been completely converted. After distilling off the solvent, 2.8 g of a colourless oil are obtained which, according to gas chromatography analysis, has a purity of 96%.

Example 4

Preparation of (1S,2S)-bis-[N-(2-diethylphosphona-toethyl)amino]cyclohexane

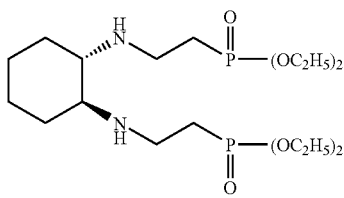

1.0 g of (1S,2S)-(−)-diaminocyclohexane (8.8 mmol) is dissolved in 10 ml of ethanol, then 2.7 ml of diethyl vinylphosphonate (2.9 g, 17.5 mmol) are added. The mixture is stirred at room temperature for 27 h. According to gas chromatography analysis, the reactant has been completely converted. After distilling off the solvent, 3.9 g of a colourless oil are obtained which, according to gas chromatography analysis, has a purity of 90%.

Example 5

Preparation of (1S,2S)-bis-[N-(2-diethylphosphona-toethyl)amino]-1,2-di-phenylethane

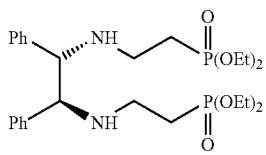

2.0 g of (1S,2S)-diphenylethylenediamine (9.4 mmol) are initially charged in 50 ml of ethanol, then 3.2 ml of diethyl vinylphosphonate (20.7 mmol) are added and the mixture is heated to reflux temperature for 72 h. The ethanol is distilled off and the residue chromatographed on silica gel. Elution with ethyl acetate/methanol (5:2) provides 2.5 g of crude product which still contains vinylphosphonic ester. This material is distilled off in a Kugelrohr at 60 to 90° C. and 0.1 mbar. The residue contains clean ligand ($^1$H NMR).

Example 6

Preparation of (1S,2S)-bis-[N-(2-carboxyethylethyl)amino]-1,2-diphenyl-ethane

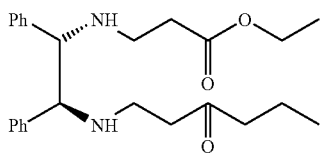

2.0 g of (1S,2S)-diphenylethylenediamine (9.4 mmol) are dissolved in 50 ml of ethanol. After adding 2.2 ml of ethyl acrylate (20.7 mmol), the mixture is stirred at room temperature for 48 h. Ethanol and excess acrylic ester are distilled off under reduced pressure. The residue remaining is the desired ligand as a homogeneous compound.

Examples 7 to 10

Asymmetric Reduction of propiophenone

A rolled flange vessel with a septum seal is evacuated and filled with argon. 0.23 mmol of a chiral ligand of Examples 1 to 6 is then weighed in and dissolved in 0.7 ml of toluene, and 0.21 ml of a 1.1 M solution of diethyizino in toluene (0.23 mmol) is added. The mixture is stirred at room temperature for 10 min, in order to form the complex from the zinc compound and the ligand. Afterwards, 1.5 ml of propiophenone (1.51 g, 11.3 mmol) and 0.90 g of polymethylhydrosiloxane (PMHS, 13.2 mmol) are added to the reaction mixture and it is stirred at 30° C. for 23 h.

For the analysis, 0.05 ml of the reaction mixture is cautiously added dropwise to 1.5 ml of 45% aqueous KOH. 4 ml of toluene are added and the reaction product is extracted into the organic phase. After removing the organic phase and drying over $MgSO_4$, gas chromatography analysis is carried out on a chiral column, a column developed for enantiomer separation of amino acids, with chemical bonding (immobilisation) of the phase in fused silica capillaries, sold under the trademark PERMABOND® L-CHIRASIL-VAL.

The results are reported in Table 1

| Example | Ligand | Yield (%) | % ee |
|---|---|---|---|
| 7 | ![cyclohexane bis(aminoethyl CN)] | 68 | 82 |
| 8 | ![diphenyl bis(aminoethyl CN)] | 58 | 82 |
| 9 | ![diphenyl bis(aminoethyl COOC2H5)] | 78 | 83 |
| 10 (noninventive) | ![diphenyl bis(N-isopropyl)] | 63 | 80 |

Examples 11 to 14

Asymmetric Reduction of Isobutyrophenone

A rolled flange vessel with a septum seal is evacuated and filled with argon. 0.20 mmol of a chiral ligand of Examples 1 to 6 is then weighed in and dissolved in 0.62 ml of toluene, and 0.185 ml of a 1.1 M solution of diethylzinc in toluene (0.20 mmol) is added. The mixture is stirred at room temperature for 10 min, in order to form the complex from the zinc compound and the ligand. Afterwards, 1.5 ml of isobutyrophenone (1.48 g, 10.0 mmol) and 0.80 g of polymethylhydrosiloxane (PMHS, 12.3 mmol) are added to the reaction mixture and it is stirred at 30° C. for 23.5 h.

For the analysis, 0.05 ml of the reaction mixture is cautiously added dropwise to 1.5 ml of 45% aqueous KOH. 4 ml of toluene are added and the reaction product is extracted into the organic phase. After removing the organic phase and drying over $MgSO_4$, gas chromatography analysis is carried out on a chiral column, a column developed for enantiomer separation of amino acids, with chemical bonding (immobilisation) of the phase in fused silica cappilaries, sold under the trademark PERMABOND® L-CHIRASIL-VAL.

The results are reported in table 2

| Example | Ligand | Yield (%) | % ee |
|---|---|---|---|
| 11 | | 64 | 83 |
| 12 | | 50 | 86 |
| 13 | | 63 | 89 |
| 14 (noninventive) | | 61 | 81 |

Examples 15 to 17

Asymmetric Reduction of 2-bromoacetophenone

A rolled flange vessel with a septum seal is evacuated and filled with argon. 0.20 mmol of a chiral ligand of Examples 1 to 6 is then weighed in and dissolved in 0.7 ml of toluene, and 0.21 ml of a 1.1 M solution of diethyizino in toluene (0.20 mmol) is added. The mixture is stirred at room temperature for 10 mm, in order to form the complex from the zinc compound and the ligand. Afterwards, 1.52 ml of 2-bromoacetophenone (2.2 g, 11.3 mmol) and 0.90 g of polymethylhydrosiloxane (PMHS, 13.2 mmol) are added to the reaction mixture and ills stirred at 30° C. for 23 h.

For the analysis, 0.05 ml of the reaction mixture is cautiously added dropwise to 1.5 ml of 45% aqueous KOH. 4 ml of toluene are added and the reaction product is extracted into the organic phase. After removing the organic phase and drying over $MgSO_4$, gas chromatography analysis is carried out on a chiral column, a column developed for enantiomer separation of amino acids, with chemical bonding (immobilisation) of the base in fused silica cappilaries, sold under the trademark PERMABOND® L-CHIRASIL-VAL.

The results are reported in Table 3

| Example | Ligand | Yield (%) | % ee |
|---|---|---|---|
| 15 | | 65 | 76 |
| 16 | | 76 | 75 |
| 17 (noninventive) | | 73 | 71 |

Examples 18 to 22

Asymmetric Reduction of 2-methylacetophenone

A rolled flange vessel with a septum seal is evacuated and filled with argon. 0.20 mmol of a chiral ligand of Examples 1 to 6 is then weighed in and dissolved in 0.62 ml of toluene, and 0.185 ml of a 1.1 M solution of dimethylzinc in toluene (0.20 mmol) is added. The mixture is stirred at room temperature for 10 min, in order to form the complex from the zinc compound and the ligand. Afterwards, 1.31 ml of 2-methylacetophenone (1.34 g, 10.0 mmol) and 0.80 g of polymethylhydrosiloxane (PMHS, 11.8 mmol) are added to the reaction mixture and it is stirred at 30° C. for 22 h.

For the analysis, 0.05 ml of the reaction mixture is cautiously added dropwise to 1.5 ml of 45% aqueous KOH. 4 ml at toluene are added and the reaction product is extracted into the organic phase. After removing the organic phase and drying over $MgSO_4$, gas chromatography analysis is carried out on a chiral column, a column developed for enantiomer separation of amino acids, with chemical bonding, (immobilisation) of the hase in fused silica capillaries, sold under the trademark PERMABOND® L-CHIRASIL-VAL.

| Example | Ligand | Yield (%) | % ee |
|---|---|---|---|
| 18 | | 85 | 57 |
| 19 | | 72 | 60 |

-continued

| Example | Ligand | Yield (%) | % ee |
|---|---|---|---|
| 20 | 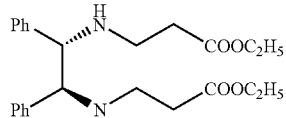 | 72 | 72 |
| 21 | 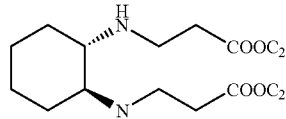 | 82 | 61 |
| 22 (noninventive) | 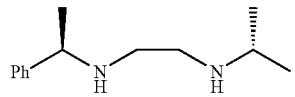 | 83 | 28 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds of the formula (I)

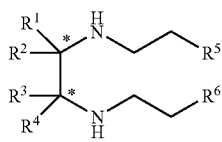

where
* marks stereogenic carbon atoms which each independently have R- or S-configuration, excluding meso-forms and
$R^1$, $R^2$, $R^3$ and $R^4$ are each independently hydrogen, $C_1$–$C_{12}$-alkyl, $C_4$–$C_{24}$-aryl or $C_5$–$C_{25}$-arylalkyl, or $R^1$, $R^2$, $R^3$ and $R^4$ together with ethylene bridge are 1,2-($C_5$–$C_8$-cycloalkyl) and
$R^5$ and $R^6$ are each independently radicals which are selected from the group of —COOR$^7$, —CONR$^8$R$^9$, —CN or —PO(OR$^{10}$)$_2$ where $R^7$, $R^8$, $R^9$ and $R^{10}$ are each $C_1$–$C_{12}$-alkyl, $C_4$–$C_{24}$-aryl or $C_5$–$C_{25}$-arylalkyl, or NR$^8$R$^9$ as a whole is a cyclic amino radical having a total of 4 to 12 carbon atoms.

2. Compounds according to claim 1, characterized in that $R^1$, $R^2$, $R^3$ and $R^4$ are each independently hydrogen, $C_1$–$C_8$-alkyl or $C_4$–$C_{24}$-aryl, or $R^1$, $R^2$, $R^3$ and $R^4$ together with the ethylene bridge are each 1,2-cyclohexylene.

3. Compounds according to claim 1, characterized in that $R^1$, $R^2$, $R^3$ and $R^4$ together with the ethylene bridge are each (R,R)- and (S,S)-1,2-diphenyl-1,2-ethylene or (R,R)- and (S,S)-1,2-cyclohexylene.

4. Compounds according to claim 1, characterized in that $R^5$ and $R^6$ are each independently selected from the group of —COOR$^7$, —CONR$^8$R$^9$, —CN or —POOR$^{10}$)$_2$ where $R^7$, $R^8$, $R^9$ and $R^{10}$ are each $C_1$–$C_4$-alkyl or $C_4$–$C_{24}$-aryl.

5. The compound of claim 1 which is (1S,2S)- and (1R,2R)-bis-[N-(2-dimethylphosphonatoethyl)amino]cyclohexane, (1S,2S)- and (1R,2R)-bis-[N-(2-diethylphosphonatoethyl)amino]-cyclohexane, (1S,2S)- and (1R,2R)-bis-[N-(2-diphenylphosphonatoethyl)amino]cyclohexane, (1S,2S)- and (1R,2R)-bis-[N-(2-cyanoethyl)amino]cyclohexane, (1S,2S)- and (1R,2R)-bis-[N-(2-carboxylethylethyl)amino]cyclohexane and (1S,2S)- and (1R,2R)-bis-[N-(2-carboxylmethylethyl)amino]-cyclohexane, (1S,2S)- and (1R,2R)-bis-[N-(2-dimethyl-phosphonatoethyl)amino]1,2-diphenylethane, (1S,2S)- and (1R,2R)-bis-[N-(2-diethylphosphonatethyl)amino]-1,2-diphenylethane, (1S,2S)- and (1R,2)-bis-[N-(2-diphenylphosphonatoethyl)amino]-1,2-diphenylethane, (1S,2S)- and (1R,2R)-bis-[N-(2-cyanoethyl)amino]-1,2-diphenylethane, (1S,2S)- and (1R,2R)-bis-[N-(2-carboxyethylethyl)amino]-1,2-diphenylethane, or (1S,2S)- and (1R,2R)-bis-[N-(2-carboxymethylethyl)amino]1,2-diphenylethane.

6. Transition metal complexes containing compounds according to claim 1.

7. Transition metal complexes according to claim 6, characterized in that the ratio of transition metal to compounds of the formula (I) is 0.5 to 1.5.

8. Transition metal complexes according to claim 6, characterized in that the compounds are zinc and cobalt complexes.

9. Transition metal complexes according to claim 6, characterized in that the transition metal complexes are obtainable by reacting halides, carbonates, cyanurates, isocyanates, sulphates, phosphates, nitrates, carboxylates or alkoxides of zinc or cobalt with a compound of the formula (I)

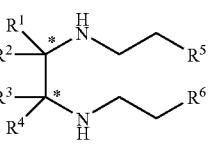

where
marks stereogenic carbon atoms which each independently have R- or S-configuration, excluding mesa-forms and
$R^1$, $R^2$, $R^3$ and $R^4$ are each independently hydrogen, $C_1$–$C_{12}$-alkyl, $C_4$–$C_{24}$-aryl or $C_5$–$C_{25}$-arylalkyl, or $R^1$, $R^2$, $R^3$ and $R^4$ together with ethylene bridge are 1,2-($C_5$–$C_8$-cycloalkyl) and
$R^5$ and $R^6$ are each independently radicals which are selected from the group of —COOR$^7$, —CONR$^5$R$^9$, —CN or —PO(OR$^{10}$)$_2$ where $R^7$, $R^3$, $R^9$ and $R^{10}$ are each $C_1$–$C_{12}$-alkyl, $C_4$–$C_{24}$-aryl or $C_5$–$C_{25}$-arylalkyl, or NR$^8$R$^9$ as a whole is a cyclic amino radical having a total of 4 to 12 carbon atoms.

10. Transition metal complexes according to claim 9, wherein a reducing agent is used in the reaction.

11. Transition metal complexes according to claim 6, characterized in that the transition metal complexes are prepared by reacting zinc compounds ZnY$_2$ or ZnYHal where Y is in each case independently hydrogen, BH$_4$ or an organic radical, and Hal is bromine, chlorine or iodine with a compound of the formula (I)

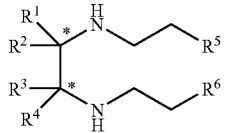
(I)

wherein
- * marks stereogenic carbon atoms which each independently have R- or S-configuration, excluding mesa-forms and
- $R^1$, $R^2$, $R^3$ and $R^4$ are each independently hydrogen, $C_1$–$C_{12}$-alkyl, $C_4$–$C_{24}$-aryl or $C_5$–$C_{25}$-arylalkyl, or $R^1$, $R^2$, $R^3$ and $R^4$ together with ethylene bridge are 1,2-($C_5$–$C_8$-cycloalkyl); and
- $R^5$ and $R^6$ are each independently radicals which are selected from the group of —$COOR^7$, —$CONR^8R^9$, —CN or —$PO(OR^{10})_2$ where $R^7$, $R^8$, $R^9$ and $R^{10}$ are each $C_1$–$C_{12}$-alkyl, $C_4$–$C_{24}$-aryl or $C_5$–$C_{25}$-arylalkyl, or $NR^8R^9$ as a whole is a cyclic amino radical having a total of 4 to 12 carbon atoms.

12. Catalysts comprising transition metal complexes according to claim 6.

13. Process for asymmetrically reducing ketones with silanes in the presence of catalysts, characterized in that the catalysts used are those according to claim 12.

14. Process according to claim 13, characterized in that the silanes used are those of the formula (V)

$$H_rSiCl_s(C_1\text{–}C_8\text{-alkyl})_t(C_1\text{–}C_8\text{-alkoxy})_u(\text{phenyl})_v \qquad (V)$$

where
r is one, two or three
and
$(s+t+u+v)=(4-r)$ or polymethylhydrosiloxane (PMHS) having the repeating structural unit

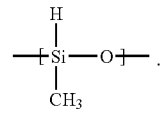

15. Process according to claim 13, characterized in that the amount of catalyst is in a molar ratio of transition metal to ketone used of 0.01 to 0.20.

16. Process according to claim 13, characterized in that the ketones used are aryl ketones.

* * * * *